United States Patent
Wang (10) Patent No.: US 11,135,199 B2
(45) Date of Patent: Oct. 5, 2021

(54) SUBLINGUAL PHARMACEUTICAL COMPOSITIONS OF EDARAVONE AND (+)-2-BORNEOL

(71) Applicant: YANTAI YENEPHARMA CO., LTD., Shandong (CN)

(72) Inventor: Yijun Wang, Jiangsu (CN)

(73) Assignees: NEURODAWN PHARMACEUTICAL CO., LTD., Jiangsu (CN); SIMCERE PHARMACEUTICAL CO., LTD., Jiangsu (CN)

( * ) Notice: Subject to any disclaimer, the term of this patent is extended or adjusted under 35 U.S.C. 154(b) by 258 days.

(21) Appl. No.: 16/326,470

(22) PCT Filed: Aug. 23, 2017

(86) PCT No.: PCT/CN2017/098620
§ 371 (c)(1),
(2) Date: Feb. 19, 2019

(87) PCT Pub. No.: WO2018/040989
PCT Pub. Date: Mar. 8, 2018

(65) Prior Publication Data
US 2020/0297697 A1    Sep. 24, 2020

(30) Foreign Application Priority Data
Aug. 29, 2016  (CN) .......................... 201610761890.7

(51) Int. Cl.
| | | |
|---|---|---|
| *A61K 31/4152* | (2006.01) | |
| *A61K 9/00* | (2006.01) | |
| *A61K 9/20* | (2006.01) | |
| *A61K 47/26* | (2006.01) | |
| *A61K 47/32* | (2006.01) | |
| *A61K 31/045* | (2006.01) | |

(52) U.S. Cl.
CPC ........ *A61K 31/4152* (2013.01); *A61K 9/0056* (2013.01); *A61K 9/20* (2013.01); *A61K 31/045* (2013.01); *A61K 47/26* (2013.01); *A61K 47/32* (2013.01)

(58) Field of Classification Search
CPC .... A61K 31/4152; A61K 9/0056; A61K 9/20; A61K 31/045; A61K 47/26; A61K 47/32
USPC ........................................................ 514/404
See application file for complete search history.

(56) References Cited

U.S. PATENT DOCUMENTS

| | | |
|---|---|---|
| 4,869,899 A | 9/1989 | Burghart et al. |
| 4,870,090 A | 9/1989 | Noda et al. |
| 8,658,684 B2 * | 2/2014 | Yin ...................... A61K 31/045 |
| | | 514/404 |
| 2011/0003873 A1 | 1/2011 | Yin et al. |
| 2015/0250856 A1 | 9/2015 | Schwarz et al. |

FOREIGN PATENT DOCUMENTS

| | | |
|---|---|---|
| CN | 1504208 A | 6/2004 |
| CN | 1739588 A | 3/2006 |
| CN | 102485223 A | 6/2012 |
| CN | 102579432 A | 7/2012 |
| JP | S63-152317 A | 6/1988 |
| JP | S63-503304 A | 12/1988 |
| JP | 2011-513249 A | 4/2011 |

OTHER PUBLICATIONS

Indian Patent Application No. 201917004777: Examination Report dated Dec. 17, 2019, 6 pages.
Japanese Patent Application No. 2019-530537: Notice of Reasons for Refusal dated Nov. 29, 2019, 6 pages.
Nippon Kayaku Co., Ltd., "0.3 mg of a Nitro-pen (R) sublingual tablet", Aug. 2014, 1-3.
Russian Patent Application No. 2019108605(016545): Official Action dated Nov. 15, 2019, 16 pages.

\* cited by examiner

*Primary Examiner* — Kristin A Vajda
(74) *Attorney, Agent, or Firm* — BakerHostetler (57) ABSTRACT

A sublingual tablet pharmaceutical composition containing edaravone and (+)-2-borneol, and a preparation method thereof. The sublingual tablet pharmaceutical composition includes edaravone, (+)-2-camphanol, an excipient, a filler, a binder, a disintegrant, and a lubricant. The excipient is selected from one or more of mannitol, lactose, dextran, cysteine, glycine, copovidone, and beta-cyclodextrin.

11 Claims, 2 Drawing Sheets

SUBLINGUAL PHARMACEUTICAL COMPOSITIONS OF EDARAVONE AND (+)-2-BORNEOL

This is a US National Phase application based upon PCT Application No. PCT/CN2017/098620, filed Aug. 23, 2017, which claims priority to Chinese Patent Application No. 2016107618907, filed on Aug. 29, 2016, and the disclosures of which are hereby incorporated by reference.

FIELD

The present disclosure belongs to the field of medicine technology, and relates to a sublingual pharmaceutical composition of edaravone and (+)-2-borneol and method for producing the same.

BACKGROUND

Edaravone (chemical name: 3-methyl-1-phenyl-2-pyrazolin-5-one) is a marketed brain neuroprotective agent (Yakugaku Zasshi. 2004, 124(3): 99-111). Studies have shown that edaravone has antioxidant activity, which can significantly improves the symptoms of neurological deficits in cerebral ischemia-reperfusion animals, reduces infarct size, reduces the degree of brain damage, reduces brain edema, and inhibits lipid peroxidation in damaged brain tissue.

Edaravone

Molecular Formula $C_{10}H_{10}N_2O$, Molecular Weight 174.20

(+)-2-Borneol is the main ingredient of a traditional Chinese medicine—natural borneol. Borneol has functions of "analepsia and resuscitation", "aromatic resuscitation" and "guiding medicine", often used as "medicinal guide" to increase the therapeutic effect of other medicine. "Augmented Materia Medica" described that borneol is "weak alone, and effective as adjuvant." Animal experiments and in vitro experiments show that borneol has the effect of promoting the drug penetration through the blood-brain barrier.

(+)-2-Borneol

Molecular Formula $C_{10}H_{18}O$; Molecular Weight 154.25

Cerebrovascular disease, especially ischemic cerebrovascular disease, is an acute disease that needs to be quickly relieved, and thus injection administration is the preferred method of first-aid. The invention patent (CN101848711A) entitled "Pharmaceutical composition and its use in the preparation of a medicament for the treatment of cerebrovascular diseases" discloses use of a composition comprising edaravone and (+)-2-borneol injection in a specific ratio in the preparation of a medicament for treating cerebrovascular diseases, particularly ischemic cerebrovascular diseases, the composition exhibiting better pharmacological results than edaravone injection.

However, intramuscular or intravenous injection can cause pain and irritation at the injunction site, and requires medical personnel to operate, and also requires injecting supplies. The application thereof is subject to certain medical restrictions and is not suitable for patients who are outside the hospital.

Sublingual preparation is directly absorbed by the sublingual mucosa. The sublingual mucosa has a large surface area and is easy to be penetrated. The sublingual mucosa has a large number of capillaries under the mucous membrane, which come together into the internal jugular vein, so that the preparation directly enters the blood circulation via superior vena cava. Thus, the drug is quickly absorbed after administration, which has advantages of fast onset, accurate quantity, convenient use, and avoiding the first-pass metabolism effect of oral drugs. Compared to injections, sublingual tablets can greatly improve the convenience of medication and clinical patient compliance.

However, sublingual pharmaceutical Compositions comprising edaravone and (+)-2-borneol are not readily available. The inventors of the present disclosure have found that common excipients are not suitable for producing acceptable edaravone and (+)-2-borneol sublingual tablets, or that the properties (stability, release rate, etc.) of the resulting sublingual tablets are not satisfying.

Therefore, there is still an urgent need in the prior art for a sublingual pharmaceutical composition comprising edaravone and (+)-2-borneol with satisfying stability and release rate.

SUMMARY

It is an object of the present disclosure to provide a sublingual pharmaceutical composition comprising edaravone or a salt thereof and (+)-2-borneol.

The volatility of (+)-2-borneol makes its content in solid preparations unstable. In addition, the ingredients of the sublingual tablet need to be released quickly to reach a certain concentration in blood to produce therapeutic effect. The inventors have unexpectedly found that the above problems can be effectively solved by using an excipient comprising a combination of mannitol and copovidone. Based on this finding, the present disclosure provides a sublingual pharmaceutical composition comprising edaravone or a salt thereof and (+)-2-borneol, in which (+)-2-borneol has a stable content and the pharmaceutically active ingredients can be quickly released and absorbed under the tongue.

In order to achieve the above object, the present disclosure adopts the following technical solutions.

A sublingual tablet comprising a composition of edaravone and (+)-2-borneol, characterized by comprising an active ingredient edaravone or a salt thereof and a pharmaceutically acceptable adjuvant, said pharmaceutically acceptable adjuvant comprises an excipient, wherein the excipient is one or more selected from the group consisting of mannitol, lactose, dextran, cysteine, glycine, copovidone and beta-cyclodextrin preferably the excipient comprises a combination of mannitol and copovidone.

In the preferred sublingual tablet pharmaceutical composition of the present disclosure, mannitol and copovidone are used as an excipient in a mass ratio of 1:5 to 5:1, preferably 1:1 to 5:1.

In some preferred embodiments of the present disclosure, the excipient comprises a combination of mannitol, copovidone and microcrystalline cellulose. Preferably, the mass ratio of mannitol, copovidone and microcrystalline cellulose is (5~10):(1~10):(10~20).

In still other preferred embodiments of the present disclosure, the excipient comprises a combination of mannitol, copovidone and lactose. Preferably, the mass ratio of mannitol, copovidone and lactose is (1~10):(1~5):(10~30).

In the sublingual tablet pharmaceutical composition, the mass ratio of edaravone in terms of free base to (+)-2-borneol is greater than 4 or less than 1, preferably, the mass ratio of edaravone in terms of free base to (+)-2-borneol is greater than 4 and less than 10 or greater than 0.1 and less than 1, and further preferably, the mass ratio of edaravone in terms of free base to (+)-2-borneol is 5.

In the sublingual tablet pharmaceutical composition, the weight ratio of (+)-2-borneol to the excipient is 0.1 to 1, preferably, the weight ratio of (+)-2-borneol to the excipient is 0.3 to 1, and more preferably; the weight ratio of (+)-2-borneol to the excipient is 0.3 to 0.5.

A method for producing the sublingual tablet pharmaceutical composition comprising the steps of dissolving (+)-2-borneol in an organic solution, and dissolving excipient in an aqueous solution; combining the two obtained solutions, stiffing and then leaving to stand; performing, freeze-drying and then sieving; adding edaravone, filler, binder, disintegrant and lubricant, and mixing until homogeneous; and tableting.

When the sublingual tablet pharmaceutical composition is administrated to a subject, within about 0.1 to 10 hours after administration of a unit of the preparation, edaravone concentration in blood reaches 10 to 8000 ng/mL, and (+)-2-borneol concentration in blood reaches 1 to 200 ng/mL, preferably, within about 0.1 to 6 hours after administration of a unit of the preparation, edaravone concentration in blood reaches 50 to 5000 ng/mL, and (+)-2-borneol concentration in blood reaches 2 to 150 ng/mL.

DETAILED DESCRIPTION

The present disclosure discloses a sublingual administration preparation of edaravone and (+)-2-borneol. Those skilled in the art can learn from the content of the present disclosure, and based on the principle of pharmacy, appropriately improve the process parameters or the prescription ratio. It is to be noted that all such alternatives and modifications are obvious to those skilled in the art and are considered to be included within the scope of the present disclosure. The application of the present disclosure has been described in preferred embodiments, and it is obvious for a person skilled in the art to change or appropriately modify and combine the to method and application described herein without departing from the scope of the present disclosure, to implement and apply the technique of the present disclosure.

The edaravone mentioned in the examples is 3-methyl-1-phenyl -2-pyrazolin-5-one.

The present disclosure is further illustrated by the following examples, but the examples are not intended to limit the present disclosure.

Example 1

| Material | Amount (g) |
|---|---|
| Edaravone | 30 |
| (+)-2-Borneol | 1.5 |
| Lactose | 39.7 |
| Hypromellose | 4 |
| Croscarmellose sodium | 4 |
| Magnesium stearate | 0.8 |

Preparation method: (+)-2-borneol, edaravone, lactose, hypromellose, croscamellose sodium, magnesium stearate were uniformly mixed and then tableted.

Example 2

| Material | Amount (g) |
|---|---|
| Edaravone | 30 |
| (+)-2-Borneol | 2 |
| Lactose | 39.2 |
| Hypromellose | 4 |
| Croscarmellose sodium | 4 |
| Magnesium stearate | 0.8 |

Preparation method: (+)-2-borneol, edaravone, lactose, hypromellose, croscarmellose sodium, magnesium stearate were uniformly mixed and then tableted.

Example 3

| Material | Amount (g) |
|---|---|
| Edaravone | 1.5 |
| (+)-2-Borneol | 30 |
| Lactose | 39.7 |
| Hypromellose | 4 |
| Croscarmellose sodium | 4 |
| Magnesium stearate | 0.8 |

Preparation method: (±)-2-borneol, edaravone, lactose, hypromellose, croscarmellose sodium, magnesium stearate were uniformly mixed and then tableted.

Example 4

| Material | Amount (g) |
|---|---|
| Edaravone | 6 |
| (+)-2-Borneol | 30 |
| Beta-cyclodextrin | 35.2 |
| Lactose | 10 |
| Hypromellose | 4 |

| Material | Amount (g) |
| --- | --- |
| Croscarmellose sodium | 4 |
| Magnesium stearate | 0.8 |

Preparation method: (+)-2-Borneol was dissolved in an ethanol solution, and beta-cyclodextrin was dissolved in an aqueous solution. The obtained two solutions were combined and stirred, and then left to stand. The resultant was subjected to freeze-drying and sieving. Edaravone, lactose, hypromellose, croscarmellose sodium and magnesium stearate were added and mixed until homogeneous, and the mixture was tableted.

Example 5

| Material | Amount (g) |
| --- | --- |
| Edaravone | 40 |
| (+)-2-Borneol | 8 |
| Beta-cyclodextrin | 23.2 |
| Lactose | 10 |
| Hypromellose | 4 |
| Croscarmellose sodium | 4 |
| Magnesium stearate | 0.8 |

Preparation method: (+)-2-Berneol was dissolved in an ethanol solution, and beta-cyclodextrin was dissolved in an aqueous solution. The obtained two solutions were combined and stirred, and then left to stand. The resultant was subjected to freeze-drying and sieving. Edaravone, lactose, hypromellose, croscarmellose sodium and magnesium stearate were added and mixed until homogeneous, and the mixture was tableted.

Example 6

| Material | Amount (g) |
| --- | --- |
| Edaravone | 30 |
| (+)-2-Borneol | 6 |
| Mannitol | 35.2 |
| Copovidone | 4 |
| Croscarmellose sodium | 4 |
| Magnesium stearate | 0.8 |

Preparation method: (+)-2-Borneol was dissolved in an ethanol solution, and mannitol in an amount of 5 times the weight of (+)-2-borneol and a small amount of copovidone were dissolved in an aqueous solution. The obtained two solutions were combined and stirred, and then left to stand. The resultant was subjected to freeze-drying and sieving. Edaravone, the remaining mannitol, copovidone, croscarmellose sodium and magnesium stearate were added and mixed until homogeneous, and the mixture was tableted.

Example 7

| Material | Amount (g) |
| --- | --- |
| Edaravone | 50 |
| (+)-2-Borneol | 5 |
| Mannitol | 16.2 |
| Copovidone | 4 |
| Croscarmellose sodium | 4 |
| Magnesium stearate | 0.8 |

Preparation method: (+)-2-Borneol was dissolved in an ethanol solution, and mannitol in an amount of 3 times the weight of (+)-2-borneol and a small amount of copovidone were dissolved in an aqueous solution. The obtained two solutions were combined and stirred, and then left to stand. The resultant was subjected to freeze-drying and sieving. Edaravone, the remaining mannitol, copovidone, croscarmellose sodium and magnesium stearate were added and mixed until homogeneous, and the mixture was tableted.

Example 8

| Material | Amount (g) |
| --- | --- |
| Edaravone | 30 |
| (+)-2-Borneol | 6 |
| Mannitol | 14 |
| Lactose | 22.2 |
| Copovidone | 3 |
| Croscarmellose sodium | 4 |
| Magnesium stearate | 0.8 |

Preparation method: (+)-2-Borneol was dissolved in an ethanol solution, and mannitol and a small amount of copolyvidone were dissolved in an aqueous solution. The obtained two solutions were combined and stirred, and then left to stand. The resultant was subjected to freeze-drying and sieving. Edaravone, lactose, copolyvidone, croscarmellose sodium and magnesium stearate were added and mixed until homogeneous, and the mixture was tableted.

Example 9

| Material | Amount (g) |
| --- | --- |
| Edaravone | 30 |
| (+)-2-Borneol | 6 |
| Mannitol | 6 |
| Lactose | 29.2 |
| Copovidone | 4 |
| Croscarmellose sodium | 4 |
| Magnesium stearate | 0.8 |

Preparation method: (+)-2-Borneol was dissolved in an ethanol solution, and mannitol and a small amount of copolyvidone were dissolved in an aqueous solution. The obtained two solutions were combined and stirred, and then left to stand. The resultant was subjected to freeze-drying and sieving. Edaravone, lactose, copolyvidone, croscarmellose sodium and magnesium stearate were added and mixed until homogeneous, and the mixture was tableted.

Example 10

| Material | Amount (g) |
| --- | --- |
| Edaravone | 30 |
| (+)-2-Borneol | 6 |
| Lactose | 31.2 |
| Copovidone | 8 |
| Croscarmellose sodium | 4 |
| Magnesium stearate | 0.8 |

Preparation method: (+)-2-Borneol was dissolved in an ethanol solution, and lactose in an amount of 5 times the weight of (+)-2-borneol and a small amount of copolyvidone were dissolved in an aqueous solution. The obtained two solutions were combined and stirred, and then left to stand. The resultant was subjected to freeze-drying and sieving. Edaravone, the remaining lactose, copolyvidone, croscarmellose sodium and magnesium stearate were added and mixed until homogeneous, and the mixture was tableted.

Example 11

| Material | Amount (g) |
| --- | --- |
| Edaravone | 12 |
| (+)-2-Borneol | 24 |
| Lactose | 31.2 |
| Copovidone | 8 |
| Croscarmellose sodium | 4 |
| Magnesium stearate | 0.8 |

Preparation method: (+)-2-Borneol was dissolved in an ethanol solution, and lactose in an amount of 1.25 times the weight of (+)-2-borneol and a small amount of copolyvidone were dissolved in an aqueous solution. The obtained two solutions were combined and stirred, and then left to stand. The resultant was subjected to freeze-drying and sieving. Edaravone, the remaining lactose, copolyvidone, croscarmellose sodium and magnesium stearate were added and mixed until homogeneous, and the mixture was tableted.

Example 12

| Material | Amount (g) |
| --- | --- |
| Edaravone | 30 |
| (+)-2-Borneol | 6 |
| Mannitol | 14 |
| Macrocrystalline cellulose | 22.2 |
| Copovidone | 3 |
| Croscarmellose sodium | 4 |
| Magnesium stearate | 0.8 |

Preparation method: (+)-2-Borneol was dissolved in an ethanol solution, and mannitol and a small amount of copolyvidone were dissolved in an aqueous solution. The obtained two solutions were combined and stirred, and then left to stand. The resultant was subjected to freeze-drying and sieving. Edaravone, microcrystalline cellulose, copolyvidone, croscarmellose sodium and magnesium stearate were added and mixed until homogeneous, and the mixture was tableted.

Example 13

| Material | Amount (g) |
| --- | --- |
| Edaravone | 30 |
| (+)-2-Borneol | 6 |
| Mannitol | 6 |
| Microcrystalline cellulose | 16.2 |
| Copovidone | 3 |
| Croscarmellose sodium | 7 |
| Silicon dioxide | 1.1 |
| Magnesium stearate | 0.7 |

Preparation method: (+)-2-Borneol was dissolved in an ethanol solution, and mannitol and copolyvidone were dissolved in an aqueous solution. The obtained two solutions were combined and stirred, and then left to stand. The resultant was subjected to freeze-drying and sieving. Edaravone, microcrystalline cellulose, croscarmellose sodium, silicon dioxide and magnesium stearate were added and mixed until homogeneous, and the mixture was tableted.

Example 14

| Material | Amount (g) |
| --- | --- |
| Edaravone | 30 |
| (+)-2-Borneol | 6 |
| Mannitol | 14 |
| Microcrystalline cellulose | 11.2 |
| Copovidone | 3 |
| Croscarmellose sodium | 4 |
| Silicon dioxide | 1.1 |
| Magnesium stearate | 0.7 |

Preparation method: (+)-2-Borneol was dissolved in an ethanol solution, and mannitol and a small amount of copolyvidone were dissolved in an aqueous solution. The obtained two solutions were combined and stirred, and then left to stand. The resultant was subjected to freeze-drying and sieving. Edaravone, microcrystalline cellulose, copolyvidone, croscarmellose sodium, silicon dioxide and magnesium stearate were added and mixed until homogeneous, and the mixture was tableted.

Example 15

Stability test and results: an appropriate amount of samples of examples 1 to 14 were packed as a final product. Samples were storage at 40° C. and 60° C. for 10 days, 30 days and 90 days. The properties, content and related substances in the samples were tested. The results are as follows:

| Examples | Storage conditions | Properties | Content (%) Edaravone | Content (%) (+)-2-Borneol | Related substances (%) |
| --- | --- | --- | --- | --- | --- |
| Example 1 | 0 day | White to off-white tablet | 99.8 | 99.5 | 0.35 |
|  | 40° C., 10 days | White to off-white tablet | 99.5 | 69.4 | 0.37 |

-continued

| Examples | Storage conditions | Properties | Content (%) Edaravone | (+)-2-Borneol | Related substances (%) |
|---|---|---|---|---|---|
| | 60° C., 10 days | While to off-white tablet | 99.4 | 48.2 | 0.45 |
| | 40° C., 30 days | White to off-white tablet | 99.5 | 57.8 | 0.38 |
| | 60° C., 30 days | White to off-white tablet | 99.4 | 38.1 | 0.44 |
| | 40° C., 90 days | White to off-white tablet | 99.0 | 15.4 | 0.45 |
| | 60° C., 90 days | White to off-white tablet | 98.9 | 10.1 | 0.51 |
| Example 2 | 0 day | White to off-white tablet | 99.7 | 101.2 | 0.45 |
| | 40° C., 10 days | White to off-white tablet | 99.8 | 71.3 | 0.38 |
| | 60° C., 10 days | White to off-white tablet | 99.5 | 60.2 | 0.44 |
| | 40° C., 30 days | While to off-white tablet | 99.7 | 54.1 | 0.46 |
| | 60° C., 30 days | White to off-white tablet | 99.6 | 43.5 | 0.47 |
| | 40° C., 90 days | White to off-white tablet | 99.2 | 16.3 | 0.53 |
| | 60° C., 90 days | White to off-white tablet | 99.1 | 12.7 | 0.62 |
| Example 3 | 0 day | White to off-white tablet | 99.7 | 100.2 | 0.49 |
| | 40° C., 10 days | White to off-white tablet | 99.5 | 71.1 | 0.56 |
| | 60° C., 10 days | White to off-white tablet | 99.4 | 62.8 | 0.48 |
| | 40° C., 30 days | White to off-white tablet | 99.2 | 59.7 | 0.52 |
| | 60° C., 30 days | White to off-white tablet | 99.5 | 34.2 | 0.50 |
| | 40° C., 90 days | White to off-white tablet | 99.1 | 21.3 | 0.62 |
| | 60° C., 90 days | White to off-white tablet | 99.3 | 18.1 | 0.78 |
| Example 4 | 0 day | White to off-white tablet | 99.7 | 99.8 | 0.48 |
| | 40° C., 10 days | White to off-white tablet | 99.8 | 99.4 | 0.49 |
| | 60° C., 10 days | White to off-white tablet | 99.7 | 99.8 | 0.51 |
| | 40° C., 30 days | White to off-white tablet | 99.4 | 99.0 | 0.44 |
| | 60° C., 30 days | White to off-white tablet | 99.5 | 98.7 | 0.53 |
| | 40° C., 90 days | White to off-white tablet | 99.2 | 98.1 | 0.54 |
| | 60° C., 90 days | White to off-white tablet | 99.3 | 98.8 | 0.61 |
| Example 5 | 0 day | White to off-white tablet | 99.7 | 100.8 | 0.47 |
| | 40° C., 10 days | White to off-white tablet | 99.4 | 101.3 | 0.48 |
| | 60° C., 10 days | White to off-white tablet | 99.6 | 101.1 | 0.48 |
| | 40° C., 30 days | White to off-white tablet | 99.8 | 100.5 | 0.39 |
| | 60° C., 30 days | White to off-white tablet | 99.5 | 100.3 | 0.44 |
| | 40° C., 90 days | White to off-white tablet | 99.2 | 99.8 | 0.43 |
| | 60° C., 90 days | White to off-white tablet | 99.1 | 99.1 | 0.54 |
| Example 6 | 0 day | White to off-white tablet | 99.8 | 99.8 | 0.55 |
| | 40° C., 10 days | White to off-white tablet | 99.2 | 99.8 | 0.60 |
| | 60° C., 10 days | White to off-white tablet | 99.8 | 99.7 | 0.54 |
| | 40° C., 30 days | White to off-white tablet | 99.7 | 99.5 | 0.58 |

-continued

| Examples | Storage conditions | Properties | Content (%) Edaravone | (+)-2-Borneol | Related substances (%) |
|---|---|---|---|---|---|
| | 60° C., 30 days | White to off-white tablet | 99.8 | 99.8 | 0.56 |
| | 40° C., 90 days | White to off-white tablet | 99.7 | 91.6 | 0.48 |
| | 60° C., 90 days | White to off-white tablet | 99.8 | 83.7 | 0.56 |
| Example 7 | 0 day | White to off-white tablet | 99.7 | 99.5 | 0.47 |
| | 40° C., 10 days | White to off-white tablet | 99.2 | 99.6 | 0.48 |
| | 60° C., 10 days | White to off-white tablet | 99.8 | 99.8 | 0.56 |
| | 40° C., 30 days | White to off-white tablet | 99.1 | 99.8 | 0.47 |
| | 60° C., 30 days | White to off-white tablet | 99.5 | 99.7 | 0.48 |
| | 40° C., 90 days | White to off-white tablet | 99.6 | 90.8 | 0.46 |
| | 60° C., 90 days | White to off-white tablet | 99.4 | 87.3 | 0.51 |
| Example 8 | 0 day | White to off-white tablet | 99.8 | 101.2 | 0.41 |
| | 40° C., 10 days | White to off-white tablet | 99.9 | 101.1 | 0.43 |
| | 60° C., 10 days | White to off-white tablet | 99.9 | 100.9 | 0.41 |
| | 40° C., 30 days | White to off-white tablet | 99.7 | 100.0 | 0.39 |
| | 60° C., 30 days | White to off-white tablet | 99.8 | 101.0 | 0.40 |
| | 40° C., 90 days | White to off-white tablet | 99.7 | 99.8 | 0.50 |
| | 60° C., 90 days | White to off-white tablet | 99.8 | 99.2 | 0.48 |
| Example 9 | 0 day | White to off-white tablet | 99.7 | 99.7 | 0.46 |
| | 40° C., 10 days | White to off-white tablet | 99.7 | 99.8 | 0.45 |
| | 60° C., 10 days | White to off-white tablet | 99.5 | 99.6 | 0.47 |
| | 40° C., 30 days | White to off-white tablet | 99.6 | 99.7 | 0.45 |
| | 60° C., 30 days | While to off-white tablet | 99.7 | 99.8 | 0.44 |
| | 40° C., 90 days | White to off-white tablet | 99.5 | 98.7 | 0.47 |
| | 60° C., 90 days | White to off-white tablet | 99.4 | 98.7 | 0.51 |
| Example 10 | 0 day | White to off-white tablet | 99.8 | 100.1 | 0.37 |
| | 40° C., 10 days | White to off-white tablet | 99.7 | 100.2 | 0.36 |
| | 60° C., 10 days | White to off-white tablet | 99.5 | 99.8 | 0.41 |
| | 40° C., 30 days | White to off-white tablet | 99.6 | 99.1 | 0.38 |
| | 60° C., 30 days | White to off-white tablet | 99.4 | 99.6 | 0.40 |
| | 40° C., 90 days | White to off-white tablet | 99.6 | 94.3 | 0.44 |
| | 60° C., 90 days | White to off-white tablet | 99.7 | 89.4 | 0.47 |
| Example 11 | 0 day | White to off-white tablet | 98.5 | 99.8 | 0.45 |
| | 40° C., 10 days | White to off-white tablet | 98.2 | 99.5 | 0.39 |
| | 60° C., 10 days | White to off-white tablet | 98.7 | 99.6 | 0.51 |
| | 40° C., 30 days | White to off-white tablet | 98.6 | 99.7 | 0.38 |
| | 60° C., 30 days | White to off-white tablet | 98.4 | 99.8 | 0.50 |

-continued

| Examples | Storage conditions | Properties | Content (%) Edaravone | (+)-2-Borneol | Related substances (%) |
|---|---|---|---|---|---|
| | 40° C., 90 days | White to off-white tablet | 98.3 | 95.7 | 0.51 |
| | 60° C., 90 days | White to off-white tablet | 98.1 | 90.7 | 0.49 |
| Example 12 | 0 day | White to off-white tablet | 99.3 | 99.3 | 0.46 |
| | 40° C., 10 days | White to off-white tablet | 99.4 | 99.5 | 0.45 |
| | 60° C., 10 days | White to off-white tablet | 99.5 | 99.7 | 0.43 |
| | 40° C., 30 days | White to off-white tablet | 99.2 | 99.6 | 0.41 |
| | 60° C., 30 days | White to off-white tablet | 99.1 | 99.3 | 0.48 |
| | 40° C., 90 days | White to off-white tablet | 99.4 | 99.4 | 0.41 |
| | 60° C., 90 days | White to off-white tablet | 99.2 | 99.7 | 0.49 |
| Example 13 | 0 day | White to off-white tablet | 99.5 | 99.5 | 0.35 |
| | 40° C., 10 days | White to off-white tablet | 99.6 | 99.4 | 0.39 |
| | 60° C., 10 days | White to off-white tablet | 99.7 | 99.7 | 0.41 |
| | 40° C., 30 days | White to off-white tablet | 99.5 | 99.6 | 0.40 |
| | 60° C., 30 days | White to off-white tablet | 99.4 | 99.4 | 0.42 |
| | 40° C., 90 days | White to off-white tablet | 99.3 | 99.8 | 0.44 |
| | 60° C., 90 days | White to off-white tablet | 99.5 | 99.4 | 0.44 |
| Example 14 | 0 day | White to off-white tablet | 99.8 | 99.2 | 0.41 |
| | 40° C., 10 days | White to off-white tablet | 99.4 | 99.4 | 0.46 |
| | 60° C., 10 days | White to off-white tablet | 99.8 | 99.5 | 0.47 |
| | 40° C., 30 days | White to off-white tablet | 99.2 | 99.6 | 0.45 |
| | 60° C., 30 days | White to off-white tablet | 99.6 | 99.3 | 0.46 |
| | 40° C., 90 days | White to off white tablet | 99.4 | 99.4 | 0.43 |
| | 60° C., 90 days | White to off-white tablet | 99.5 | 99.7 | 0.47 |

The above data of the qualitative test results of the examples show that each of examples 4 to 14 stored at a high temperature for 30 days exhibited a good stability. Among them, examples 8, 12, 13 and 14 stored at a high temperature for 90 days exhibited a good stability.

Example 16

Dissolution Rate Test

Figure 1:
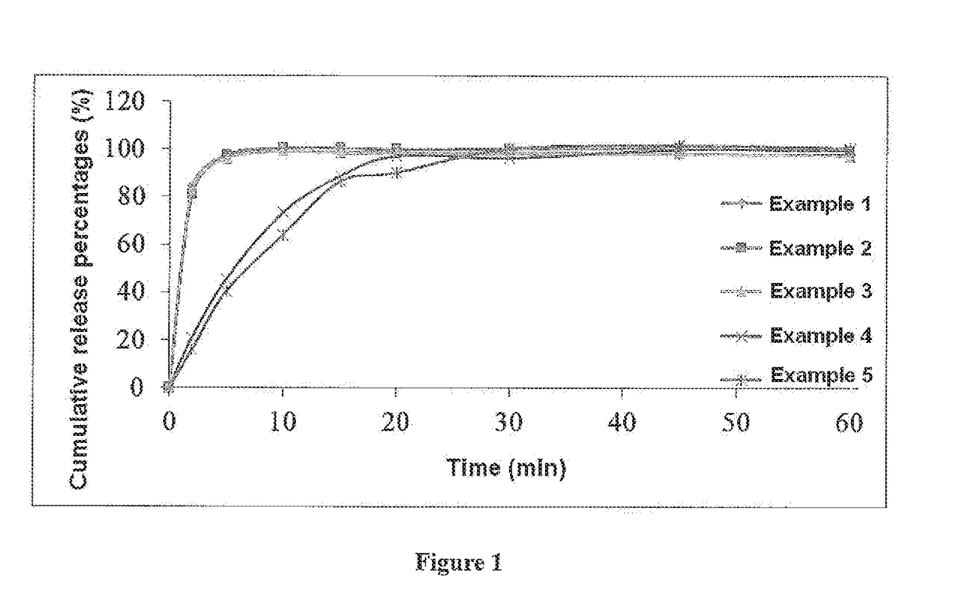
FIG. 1 is the dissolution profile of examples 1 to 5.
Figure 2:
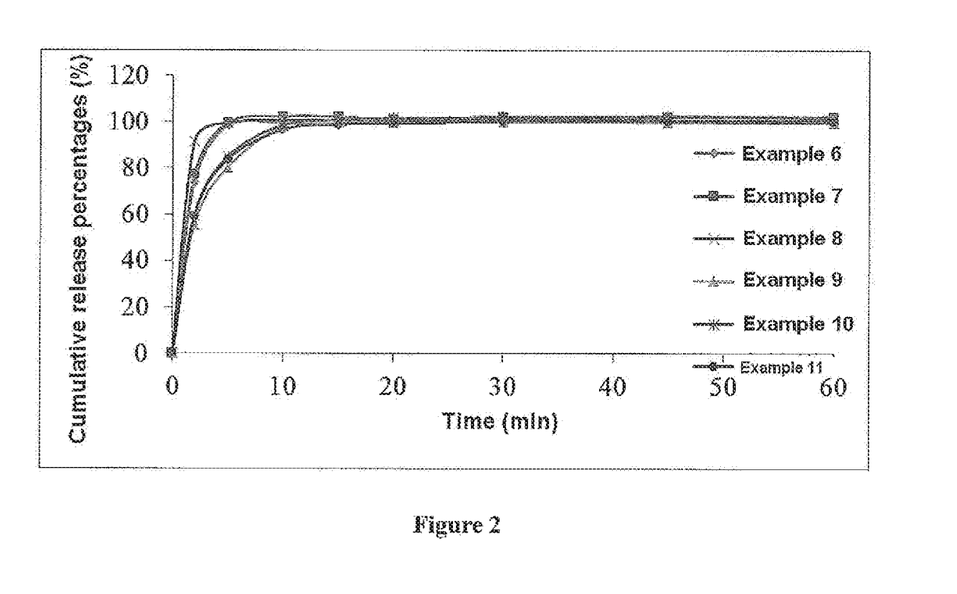
FIG. 2 is the dissolution profile of examples 6 to 11.
Figure 3:
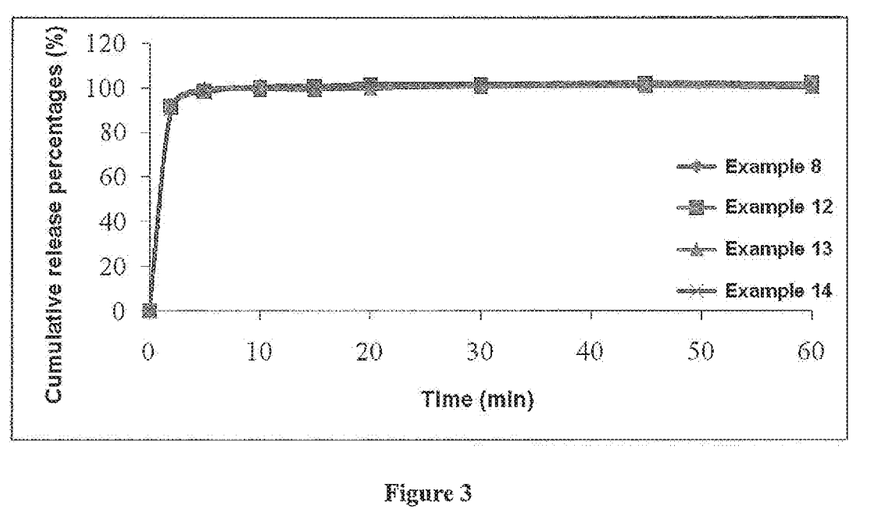
FIG. 3 is the dissolution profile of examples 8, and 12 to 14.

According to the dissolution and release test method in "Chinese Pharmacopoeia" 2015 version (the fourth part 0931, the second method), 900 ml of water was used as dissolution medium (wherein for examples 3 and 4, 250 ml of water was used as dissolution medium), under a rotating speed of 50 rpm, test was operated according to regulations. Samples were collected at different time points, filtered through 0.8 μm filter, and the subsequent filtrates were used as the test solution. Appropriate amount of edaravone reference substance was taken and dissolved in 20 mmol/L ammonium acetate/acetonitrile (80:20) solution, and then diluted to approximately 0.02 mg/ml for use. The UV absorbance of the test solution was measured at 254 nm, and the dissolution rate of the sample was calculated. The results are shown in FIGS. 1, 2 and 3

Example 17

Distribution of edaravone in plasma and brain tissue of SD rats after sublingual administration 1. Materials and Methods 1.1 Experimental Animals Sprague-Dawley (SD) rats, SPF grade, male, weight 180-200 g.
Source: Beijing Weitong Lihua Experimental Animal Technology Co., Ltd.
Certificate number: 11400700138404
License number: SCXK (Beijing) 2012-0001
Foods and water supply: Rats were fasted for 12 h before the test, and foods were supplied 4 h after the administration.

Water was not prohibited throughout the experiment. Abnormalities of the animals were observed and recorded during drug administration and sample collecting.

1.2 Test Drugs

Compound edaravone injection: specification 12.5 mg/5 mL (edaravone and (+)-2-borneol were 10 mg/5 mL and 2.5 mg/5 mL, respectively).

Sublingual tablets prepared according to the formulation ratio of Example 8, each containing 5 mg of edaravone and 1 mg of borneol.

1.3 Methods

Group 1: Intravenous administration of compound edaravone injection (N=4)

Dosage: 16 mg/kg edaravone, 4 mg/kg, (+)-2-borneol; administration volume: 8 mL/kg. Plasma and brain tissue samples were collected at 2 min, 15 min, 30 min, 1 h, 2.5 h and 5 h. At each time point, whole blood and brain tissue were collected simultaneously.

Group 2: one sublingual tablet was given under the tongue (N=6).

SD rats were intraperitoneal injected with chloral hydrate to make SD rats under mild anesthesia, The mouth of rat was moistened with 50 μL of water, and one tablet was inserted under the tongue of the rat, 1 tablet/rat. The mouth was fixed for 30 min to prevent the tablet from falling off or sliding into the gastrointestinal tract. Taking the time of inserting the tablet under the tongue as the time point of 0 min, the whole blood and brain tissue were collected, at 5 min, 15 min, 30 min, 1 h, 2.5 h and 5 h.

2. Experimental Results

Average of each pharmacokinetic parameter of edaravone in the plasma from SD rats after intravenous administration with compound edaravone injection and SD rats administrated with sublingual tablet are shown below.

|  | Intravenous administration | Sublingual administration |
| --- | --- | --- |
| Tmax (h) | 0.033 | 2.5 |
| Cmax (ng/mL) | 58550 | 4793 |
| $AUC_{0-5\,h}$ (h*ng/mL) | 18179 | 15638 |
| MRTlast (h) | 0.59 | 2.06 |
| F (%) | / | 62.6 |

Average of each pharmacokinetic parameter of edaravone in the brain homogenate from SD rats after intravenous administration with compound edaravone injection and SD rats administrated with sublingual tablet are shown below.

|  | Intravenous administration | Sublingual administration |
| --- | --- | --- |
| Tmax (h) | 0.033 | 0.25 |
| Cmax (ng/mL) | 1405 | 55.3 |
| $AUC_{0-5\,h}$ (h*ng/mL) | 270 | 106 |
| MRTlast (h) | 0.20 | 1.18 |
| F (%) | / | 28.5 |

Average of each pharmacokinetic parameter of borneol in the plasma from SD rats after intravenous administration with compound edaravone injection and SD rats administrated with sublingual tablet are shown below.

|  | Intravenous administration | Sublingual administration |
| --- | --- | --- |
| Tmax (h) | 0.033 | 1.00 |
| Cmax (ng/mL) | 1611 | 105 |
| $AUC_{0-5\,h}$ (h*ng/mL) | 622 | 353 |
| MRTlast (h) | 0.64 | 1.86 |
| F (%) | / | 51.6 |

Average of each pharmacokinetic parameter of borneol in the brain homogenate from SD rats after intravenous administration with compound edaravone injection and SD rats administrated with sublingual tablet are shown below.

|  | Intravenous administration | Sublingual administration |
| --- | --- | --- |
| Tmax (h) | 0.033 | 0.5 |
| Cmax (ng/mL) | 5726 | 260 |
| $AUC_{0-5\,h}$ (h*ng/mL) | 1686 | 529 |
| MRTlast (h) | 0.34 | 1.31 |
| F (%) | / | 28.5 |

The results of the distribution of the ingredients in the sublingual tablet in plasma and brain tissue of SD rats showed that the bioavailability of edaravone and (+)-2-borneol in the sublingual preparation was as follows: edaravone about 62.6%, (+)-2-borneol about 51.6%; the bioavailability in the brain was as follows: edaravone about 28.5%, (+)-2-borneol about 28.5%, indicating that the bioavailability of edaravone and borneol by sublingual administration was high, satisfying sublingual administration requirements.

The sublingual tablets containing edaravone and (+)-2-borneol had advantages of good pharmacokinetic properties, high bioavailability, high brain permeability, and convenient administration.

Example 18

Protective effect of sublingual administration on focal cerebral ischemia-reperfusion 1 Materials and Methods 1.1 Experimental Animals Sprague-Dawley (SD) rat, male, clean grade, weight 260-280 g 1.2 Test Drugs Sublingual tablets were prepared according to the ratio of Example 8 in three specifications: 0.67 mg of edaravone and 0.13 mg of borneol (3 mg kg dose group); 2.01 mg of edaravone and 0.39 mg of borneol (9 mg/kg dose group); 6 mg of edaravone and 1.2 mg of borneol (27 mg/kg dose group).

Compound edaravone injection, specification; 5 mL:12.5 mg, produced by Nanjing Xiansheng Dongyuan Pharmaceutical Co., Ltd.

1.3 Experimental Methods 1.3.1 Preparation of Focal Cerebral Ischemia Reperfusion Model A cerebral ischemia reperfusion model was established by middle cerebral artery occlusion (MCAO) through internal carotid artery suture. After being anesthetized with 7% hydrated trichloroacetaldehyde (6 ml/kg) the animals were fixed on the operating table in prone position, the skin was disinfected, the neck was open, in the middle, and right common carotid artery, external carotid artery and internal carotid artery were separated, vagus nerve was gently removed, the external carotid artery was ligated, and by following the internal carotid artery, the pterygopalatine artery was ligated. The end of the common carotid artery proximity to the heart was clamped, and an incision was made from the distal end of the ligature line of the external carotid artery, into which a nylon catheter with an outer diameter of 0.285 mm was inserted. The nylon catheter entered into the internal carotid artery through bifurcation of the common carotid artery, and was slowly inserted until there was slight resistance (about 20 mm from the bifurcation). All blood supply to the middle cerebral artery was blocked. After the right cerebral suffered from ischemia for 2 h, the nylon catheter was gently puffed out, blood supply was restored for reperfusion, and the skin was sutured, and disinfected.

1.3.2 Animal Grouping and Administration

The experimental animals were divided into 5 groups: three groups of sublingual tablet (dose 3 mg/kg, 9 mg/kg, 27 mg/kg), positive drug compound edaravone group (3 mg/kg) and model group. After the preparation of the cerebral ischemia model, the animals were randomly assigned to each group. The animals in the sublingual tablet group were administered sublingual tablets with corresponding specification simultaneously with reperfusion, 1 tablet/rat, and the mouths were fixed to prevent the tablets from falling off or sliding into the gastrointestinal tract until the tablets were completely absorbed. The animals in the positive drug group were intravenously administered once immediately after reperfusion, and the animals in the model group were administered with an equal volume of physiological saline. The symptoms of neurological deficit were evaluated 24 hours after cerebral ischemia, and then the animals were sacrificed, the brains were taken out and subjected to staining and imaging to determine the area of cerebral infarction.

13.3 Neurological Deficit Scoring and Cerebral Infarct Size Measurement

Neurological deficit was evaluated using the modified Bederson 5-score scale. The symptoms of neurological deficit in rats after cerebral ischemia were evaluated by single-blind method. Specifically, the test designer marked the animals in groups. The one who scored the symptoms of neurological defects did not know the grouping of the animals. After the scoring was over, the score results of various markers were submitted to the test designer, and the designer disclosed the score for each animal of each test group.

| Annexed table: Assessment of Neurological Deficit (Bederson Scores) |
| --- |
| 0: When the tail is lifted and the body is hung in the air, the animal's forelimbs extend to the floor and there is no other behavioral deficit. |
| 1: When the tail is lifted and the body is hung in the air, the animal's forelimbs on the contralateral (left) side of the surgery show wrist flexion, shoulder rotation, elbow abduction, and close to the chest wall. |
| 2: The animal is placed on a smooth plate and the resistance reduces when pushed the shoulder in the surgical side to move to the contralateral side. |
| 3: When the animal walks freely, it will circle or wind to the contralateral side of the surgery. |
| 4: The limbs are soft and have no spontaneous activity. |

Determination of the degree of cerebral infarction

After the animal was sacrificed, the brain were removed following decapitation, the olfactory bulb, cerebellum and low brain stem were removed. The blood on the surface of the brain was washed with physiological saline, and the residual water on the surface was removed. The brain was placed at −20° C. for 20 min. Immediately after removal, the plane intersected with the line of sight was cut vertically downwards to get a coronal section, and one slice every 2 mm backward was cut. The brain slices were incubated in 2% TTC dye solution (37° C. for 90 min) for staining. The normal brain tissue was stained dark red, and the ischemic tissue was in pale color. After washed with physiological saline, the brain slices were quickly arranged in a row from front to back, and the residual water on the surface were removed, and then photographed.

The images were processed by image analysis software, and the corresponding volume of the left brain and the infarct volume were calculated according to formula, and the percentage of infarct was determined.

Calculation of infarct volume:

$$V = t(A1 + A2 + A3 + \ldots + An)$$

t is the slice thickness and A is the infarct area.

$$\% I = 100\% \times (VC - VL)/VC$$

% I is the percentage of infarct, volume, VC is the brain volume of the control side (left hemisphere), and VL is the volume of the non-infarct area of the infarct (right hemisphere).

2 Experimental Results

2.1 Effects on the Neurological Deficit

The degree of neurological deficit in each group of animals was shown in Table 1. Compared with the model group, the three doses (3, 9, 27 mg/kg) of the sublingual tablet and the positive drug compound edaravone (3 mg/kg) both significantly ameliorated the neurological deficit.

Table 1. Effects of sublingual administration of edaravone and (+)-2-borneol on the neurological deficit.

TABLE 1

| Effects of sublingual administration of edaravone and (+)-2-borneol on the neurological deficit | | |
| --- | --- | --- |
| Groups | Number of animals | Scores of neurological deficit |
| Model group | 12 | 2.58 ± 0.51 |
| Compound edaravone group | 13 | 1.77 ± 0.93* |
| Sublingual tablet (0.8 mg) | 14 | 2.00 ± 0.68* |
| Sublingual tablet (2.4 mg) | 12 | 1.75 ± 0.75** |
| Sublingual tablet (7.2 mg) | 13 | 1.54 ± 1.05** |

X ± SD. Compared to the model group, *p < 0.05, **p < 0.01.

2.2 Effects on the Area of Cerebral Infarction

The effects on the area of cerebral infarction were shown in Table 2. Compared with the model group, the three doses (3, 9, 27 mg/kg) of sublingual tablet and the positive drug compound edaravone both significantly reduced the size of the cerebral infarction area in ischemia-reperfusion animal model.

TABLE 2

Effects of sublingual administration of edaravone and (+)-2-borneol on the area of cerebral infarction

| Groups | Number of animals | Area of cerebral infarction (%) |
|---|---|---|
| Model group | 12 | 35.1 ± 11.5 |
| Compound edaravone group | 13 | 22.9 ± 13.0* |
| Sublingual tablets (0.8 mg) | 14 | 24.0 ± 10.0* |
| Sublingual tablets (2.4 mg) | 12 | 22.0 ± 11.4* |
| Sublingual tablets (7.2 mg) | 13 | 20.7 ± 13.1** |

X ± SD. Compared to the model group, *$p < 0.05$, **$p < 0.01$.

Example 19

Study on the distribution of edaravone in plasma and brain tissue of SD rats after sublingual administration:

3. Materials and Methods 1.4 Experimental Animals

Sprague-Dawley (SD) rats, SPF grade, male, weight 180-200 g.
Source: Beijing Weitong Lihua Experimental Animal Technology Co., Ltd.
Certificate number: 11400700138404.
License number: SCXK (Beijing) 2012-0001.
Foods and water supply: Rats were fasted for 12 h before the test, and foods were supplied 4 h after the administration. Water was not prohibited throughout the experiment. Abnormalities of the animals were observed and recorded during drug administration and sample collecting.

1.5 Test Drugs

Compound edaravone injection: specification 12.5 mg/5 mL (edaravone and (+)-2-borneol were 10 mg/5 mL and 2.5 mg/5 mL, respectively).
Sublingual tablets prepared according to the formulation ratio of Example 13, each containing 5 mg of edaravone and 1 mg of borneol.

1.6 Methods

Group 1: Intravenous administration of compound edaravone injection (N=4)
Dosage: 16 mg/kg edaravone, 4 mg/kg (+)-2-borneol; administration volume: 8 mL/kg. Plasma and brain tissue samples were collected at 2 min, 15 min, 30 min, 1 h, 2.5 h and 5 h. At each time point, whole blood and brain tissue were collected simultaneously.
Group 2: one sublingual tablet was given under the tongue (N=6).
SD rats were intraperitoneal injected with chloral hydrate to make SD rats under mild anesthesia. The mouth of rat was moistened with 50 μL of water, and one tablet was inserted under the tongue of the rat, 1 tablet/rat. The mouth was fixed for 30 min, to prevent the tablet from falling off or sliding into the gastrointestinal tract. Taking the time of inserting the tablet under the tongue as the time point of 0 min, the whole blood and brain tissue were collected at 5 min, 15 min, 30 min, 1 h, 2.5 h and 5 h.

4. Experimental Results

Average of each pharmacokinetic parameter of edaravone in the plasma from SD rats after intravenous administration with compound edaravone injection and SD rats administrated with sublingual tablet are shown below.

|  | Intravenous administration | Sublingual administration |
|---|---|---|
| Tmax (h) | 0.032 | 0.5 |
| Cmax (ng/mL) | 56370 | 5875 |
| $AUC_{0-5\ h}$ (h*ng/mL) | 16038 | 17427 |
| MRTlast (h) | 0.59 | 2.63 |
| F (%) | / | 79.9 |

Average of each pharmacokinetic parameter of edaravone in the brain homogenate from SD rats after intravenous administration with compound edaravone injection and SD rats administrated with sublingual tablet are shown below.

|  | Intravenous administration | Sublingual administration |
|---|---|---|
| Tmax (h) | 0.032 | 0.25 |
| Cmax (ng/mL) | 13.98 | 59.2 |
| $AUC_{0-5\ h}$ (h*ng/mL) | 255 | 110 |
| MRTlast (h) | 0.20 | 1.16 |
| F (%) | / | 30.1 |

Average of each pharmacokinetic parameter of borneol in the plasma from SD rats after intravenous administration with compound edaravone injection and SD rats administrated with sublingual tablet are shown below.

|  | Intravenous administration | Sublingual administration |
|---|---|---|
| Tmax (h) | 0.032 | 1.00 |
| Cmax (ng/mL) | 1571 | 114 |
| $AUC_{0-5\ h}$ (h*ng/mL) | 593 | 392 |
| MRTlast (h) | 0.63 | 1.93 |
| F (%) | / | 60.1 |

Average of each pharmacokinetic parameter of borneol in the brain homogenate from SD rats after intravenous administration with compound edaravone injection and SD rats administrated with sublingual tablet are shown below.

|  | Intravenous administration | Sublingual administration |
|---|---|---|
| Tmax (h) | 0.032 | 0.5 |
| Cmax (ng/mL) | 5430 | 273 |
| $AUC_{0-5\ h}$ (h*ng/mL) | 1729 | 541 |
| MRTlast (h) | 0.34 | 1.30 |
| F (%) | / | 29.6 |

The results of the distribution of the ingredients in the sublingual tablet in plasma and brain tissue of SD rats showed that the bioavailability of edaravone and (+)-2-borneol in the sublingual preparation was as follows: edaravone about 79.9%, (+)-2-borneol about 60.1%; the bioavailability in the brain was as follows: edaravone about 30.1%, (+)-2,-borneol about 29.6%, indicating that the bioavailability of edaravone and borneol by sublingual administration was high, satisfying sublingual administration requirements.

The sublingual tablets containing edaravone and (+)-2-borneol had advantages of good pharmacokinetic properties, high bioavailability, high brain permeability, and convenient administration.

Example 20

Protective effect of sublingual administration on focal cerebral ischemia-reperfusion 1 Materials and Methods 1.1 Experimental Animals Sprague-Dawley (SD) rat, male, clean grade, weight 260-280 g 1.2 Test Drugs Sublingual tablets were prepared according to the ratio of Example 13 in three specifications: 0.67 mg of edaravone and 0.13 mg of borneol (3 mg/kg dose group); 2.01 mg of edaravone and 0.39 mg of borneol (9 mg/kg dose group); 6 mg of edaravone and 1.2 mg of borneol (27 mg/kg dose group).

Compound edaravone injection, specification: 5 mL:12.5 mg, produced by Nanjing Xiansheng Dongyuan Pharmaceutical Co., Ltd.

1.3 Experimental Methods 1.3.1 Preparation of Focal Cerebral Ischemia Reperfusion Model A cerebral ischemia reperfusion model was established by middle cerebral artery occlusion (MCAO) through internal carotid artery suture. After being anesthetized with 7% hydrated, trichloroacetaldehyde (6 ml/kg), the animals were fixed on the operating table in prone position, the skin was disinfected, the neck was open in the middle, and right common carotid artery, external carotid artery and internal carotid artery were separated vagus nerve was gently removed, the external carotid artery was ligated, and by following the internal carotid artery, the pterygopalatine artery was ligated. The end of the common carotid artery proximity to the heart was clamped, and an incision was made from the distal end of the ligature line of the external carotid artery, into which a nylon catheter with an outer diameter of 0.285 mm was inserted. The nylon catheter entered into the internal carotid artery through bifurcation of the common carotid artery, and was slowly inserted until there was slight resistance (about 20 mm from the bifurcation). All blood supply to the middle cerebral artery was blocked. After the right cerebral suffered from ischemia for 2 h, the nylon catheter was gently pulled out, blood supply was restored for reperfusion, and the skin was sutured, and disinfected.

1.3.2 Animal Grouping and Administration

The experimental animals were divided into 5 groups: three groups of sublingual tablet (dose 3 mg/kg, 9 mg/kg, 27 mg/kg), positive drug compound edaravone group (3 mg/kg) and model group. After the preparation of the cerebral ischemia model, the animals were randomly assigned to each group. The animals in the sublingual tablet group were administered sublingual tablets with corresponding specification simultaneously with reperfusion, 1 tablet/rat, and the mouths were fixed to prevent the tablets from falling off or sliding into the gastrointestinal tract until the tablets were completely absorbed. The animals in the positive drug group were intravenously administered once immediately after reperfusion, and the animals in the model group were administered with an equal volume of physiological saline. The symptoms of neurological deficit were evaluated 24 hours after cerebral ischemia, and then the animals were sacrificed, the brains were taken out and subjected to staining and imaging to determine the area of cerebral infarction.

1.3.3 Neurological Deficit Scoring and Cerebral Infarct Size Measurement

Neurological deficit was evaluated using the modified Bederson 5-score scale. The symptoms of neurological deficit in rats after cerebral ischemia were evaluated by single-blind method. Specifically, the test designer marked the animals in groups. The one who scored the symptoms of neurological defects did not know the grouping of the animals. After the scoring was over, the score results of various markers were submitted to the designer, and the test designer disclosed the score for each animal of each test group.

Annexed table: Assessment of Neurological Deficit (Bederson Scores)

0: When the tail is lifted and the body is hung in the air, the animal's forelimbs extend to the floor and there is no other behavioral deficit.
1: When the tail is lifted and the body is hung in the air, the animal's forelimbs on the contralateral (left) side of the surgery show wrist flexion, shoulder rotation, elbow abduction, and close to the chest wall.
2: The animal is placed on a smooth plate and the resistance reduces when pushed the shoulder in the surgical side to move to the contralateral side.
3: When the animal walks freely, it will circle or wind to the contralateral side of the surgery.
4: The limbs are soft and have no spontaneous activity.

Determination of the Degree of Cerebral Infarction

After the animal was sacrificed, the brain were removed following decapitation, the olfactory bulb, cerebellum and low brain stem were removed. The blood on the surface of the brain was washed with physiological saline, and the residual water on the surface was removed. The brain was placed at −20° C. for 20 min. Immediately after removal, the plane intersected with the line of sight was cut vertically downwards to get a coronal section, and one slice every 2 mm backward was cut. The brain slices were incubated in 2% TTC dye solution (37° C. for 90 min) for staining. The normal brain tissue was stained dark red, and the ischemic brain tissue was in to pale color. After washed with physiological saline, the brain slices were quickly arranged in a row from front to back, and the residual water on the surface were removed, and then photographed.

The images were processed by image analysis software, and the corresponding volume of the left brain and the infarct volume were calculated according to formula, and the percentage of infarct volume was determined.

Calculation of infarct volume;

$$V=t(A1+A2+A3\ldots+An)$$

t is the slice thickness and A is the infarct area.

$$\% I=100\%\times(VC-VL)/VC$$

% I is the percentage of infarct volume, VC is the brain volume of the control side (left hemisphere), and VL is the volume of the non-infarct area of the infarct side (right hemisphere).

2 Experimental Results 2.1 Effects on the Neurological Deficit

The degree of neurological deficit in each group of animals was shown in Table 3. Compared with the model group, the three doses (3, 9, 27 mg/kg) of the sublingual tablet and the positive drug compound edaravone (3 mg/kg) both significantly ameliorated the neurological deficit.

TABLE 3

Effects of sublingual administration of edaravone and (+)-2-borneol on the neurological deficit

| Groups | Number of animals | Scores of neurological deficit |
|---|---|---|
| Model group | 11 | 2.64 ± 0.42 |
| Compound edaravone group | 12 | 1.74 ± 0.71* |
| Sublingual tablets (0.8 mg) | 14 | 2.35 ± 0.73* |
| Sublingual tablets (2.4 mg) | 14 | 1.83 ± 0.77** |
| Sublingual tablets (7.2 mg) | 13 | 1.43 ± 0.95** |

X ± SD. Compared to the model group, *p < 0.05, **p < 0.01.

2.2 Effects on the Area of Cerebral Infarction

The effects on the area of cerebral infarction were shown in Table 4. Compared with the model group, the three doses (3, 9, 27 mg/kg) of sublingual tablet and the positive drug compound edaravone both significantly reduced the size of the cerebral infarction area in ischemia-reperfusion animal model.

Table 4. Effects of sublingual administration of edaravone and (+)-2-borneol on the area of cerebral infarction.

TABLE 4

Effects of sublingual administration of edaravone and (+)-2-borneol on the area of cerebral infarction

| Groups | Number of animals | Area of cerebral infarction (%) |
|---|---|---|
| Model group | 11 | 37.2 ± 12.3 |
| Compound edaravone group | 12 | 21.6 ± 12.5* |
| Sublingual tablets (0.8 mg) | 14 | 23.4 ± 9.3* |
| Sublingual tablets (2.4 mg) | 14 | 21.3 ± 8.5* |
| Sublingual tablets (7.2 mg) | 13 | 19.8 ± 10.1** |

X ± SD. Compared to the model group, *p < 0.05, **p < 0.01.

The experimental data showed that the sublingual tablet of the present disclosure can achieve a drug effect comparable to that of an injection.

What is claimed is:

1. A sublingual tablet pharmaceutical composition comprising edaravone, (+)-2-borneol and a pharmaceutically acceptable adjuvant, wherein the pharmaceutically acceptable adjuvant comprises an excipient, and wherein the excipient comprises one or more selected from the group consisting of mannitol, lactose, dextran, cysteine, glycine, copovidone and beta-cyclodextrin.

2. The pharmaceutical composition according to claim 1, comprising mannitol and copovidone at a mass ratio of 1:5 to 5:1 as excipients.

3. The pharmaceutical composition according to claim 2, comprising mannitol and copovidone at a mass ratio of 1:1 to 5:1 as excipients.

4. The pharmaceutical composition according to claim 1, wherein the mass ratio of edaravone in terms of free base to (+)-2-borneol is greater than 4 and less than 10 or greater than 0.1 and less than 1.

5. The pharmaceutical composition according to claim 1, wherein the mass ratio of edaravone in terms of free base to (+)-2-borneol is 5:1.

6. The pharmaceutical composition according to claim 1, wherein the weight ratio of (+)-2-borneol to the excipient is from 0.1:1 to 1:1.

7. The pharmaceutical composition according to claim 1, wherein the weight ratio of (+)-2-borneol to the excipient is from 0.3:1 to 1:1.

8. A method for preparing the pharmaceutical composition according to claim 1, comprising
dissolving (+)-2-borneol in an organic solution, and dissolving the excipient in an aqueous solution; combining the two solutions and stirring, allowing the mixed solution to stand; performing freeze-drying and then sieving; adding edaravone, filler, binder, disintegrant and lubricant, and mixing until homogeneous; and tableting.

9. The pharmaceutical composition according to claim 1, wherein within about 0.1 to 10 hours after administration of a unit of the sublingual tablet to a patient, edaravone concentration in blood reaches 10 to 8000 ng/mL, and (+)-2-borneol concentration in blood reaches 1 to 200 ng/mL.

10. The pharmaceutical composition according to claim 1, wherein within about 0.1 to 6 hours after administration of a unit of the sublingual tablet to a patient, edaravone concentration in blood reaches 50 to 5000 ng/mL, and (+)-2-borneol concentration in blood reaches 2 to 150 ng/mL.

11. The pharmaceutical composition according to claim 1, comprising an adjuvant selected from mannitol and copovidone.

* * * * *